(12) United States Patent
Guo et al.

(10) Patent No.: US 9,690,534 B1
(45) Date of Patent: Jun. 27, 2017

(54) WEARABLE COMPUTING EYEGLASSES THAT PROVIDE UNOBSTRUCTED VIEWS

(71) Applicant: International Business Machines Corporation, Armonk, NY (US)

(72) Inventors: Shang Q. Guo, Cortlandt Manor, NY (US); Jonathan Lenchner, North Salem, NY (US); Maharaj Mukherjee, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/967,658

(22) Filed: Dec. 14, 2015

(51) Int. Cl.
*G06F 3/14* (2006.01)
*G02B 27/01* (2006.01)
*H04W 84/18* (2009.01)

(52) U.S. Cl.
CPC ....... *G06F 3/1423* (2013.01); *G02B 27/0172* (2013.01); *G06F 3/1415* (2013.01); *G06F 3/1462* (2013.01); *G02B 2027/0138* (2013.01); *H04W 84/18* (2013.01)

(58) Field of Classification Search
CPC .......... G06F 3/14–3/1462; G06F 3/005; G06F 3/012; G02B 27/0172; G02B 2027/0138; H04W 84/18
See application file for complete search history.

(56) References Cited

U.S. PATENT DOCUMENTS

| 7,855,638 | B2 | 12/2010 | Huston |
| 8,482,859 | B2 | 7/2013 | Border et al. |
| 8,836,771 | B2* | 9/2014 | Strong ................. G01C 21/165 348/53 |
| 9,026,596 | B2 | 5/2015 | Perez et al. |
| 2011/0254829 | A1 | 10/2011 | Agevik et al. |
| 2012/0320013 | A1* | 12/2012 | Perez ........................ H04N 5/91 345/207 |
| 2013/0021374 | A1 | 1/2013 | Miao et al. |
| 2013/0083011 | A1* | 4/2013 | Geisner ..................... G09G 5/00 345/419 |
| 2014/0184589 | A1* | 7/2014 | Vesely .................... G06F 3/012 345/419 |
| 2016/0217616 | A1* | 7/2016 | Kraver .................... G06F 3/012 |

FOREIGN PATENT DOCUMENTS

| EP | 2843508 A1 | 8/2014 | |
| JP | 2012209896 A1 * | 10/2012 | ............. H04N 5/232 |
| WO | 2013012603 A2 | 1/2013 | |

OTHER PUBLICATIONS

"CORNAR: Looking Around Corners Using Femto-Photography," http://web.media.mit.edu/~raskar/cornar, Nov. 11, 2015, 6 pages.

* cited by examiner

*Primary Examiner* — Larry Sternbane
(74) *Attorney, Agent, or Firm* — Alexa L. Ashworth; Ryan, Mason & Lewis, LLP

(57) ABSTRACT

A method for displaying a view of a target comprises establishing a network including a plurality of display devices, requesting by a first display device in the network having an obstructed view of the target, at least one of position and orientation data from one or more remaining display devices in the network each having a different view of the target than the obstructed view, selecting a remaining display device as a view provider to provide the different view of the target to the first display device, requesting the different view of the target from the selected view provider; providing the different view of the target to the first display device, and displaying the different view of the target via the first display device.

18 Claims, 10 Drawing Sheets

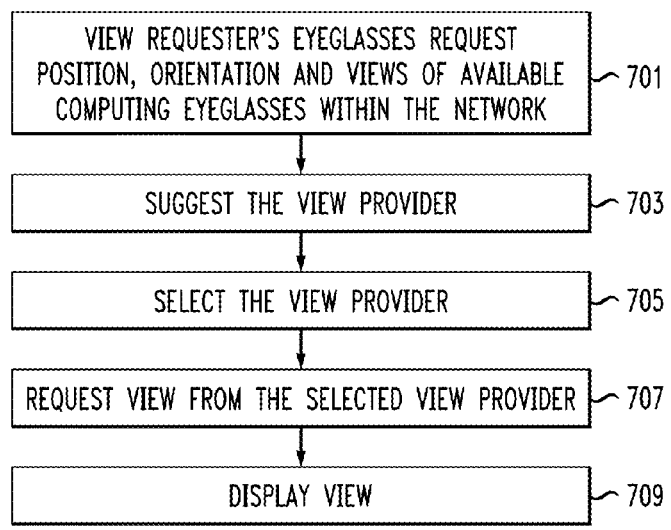
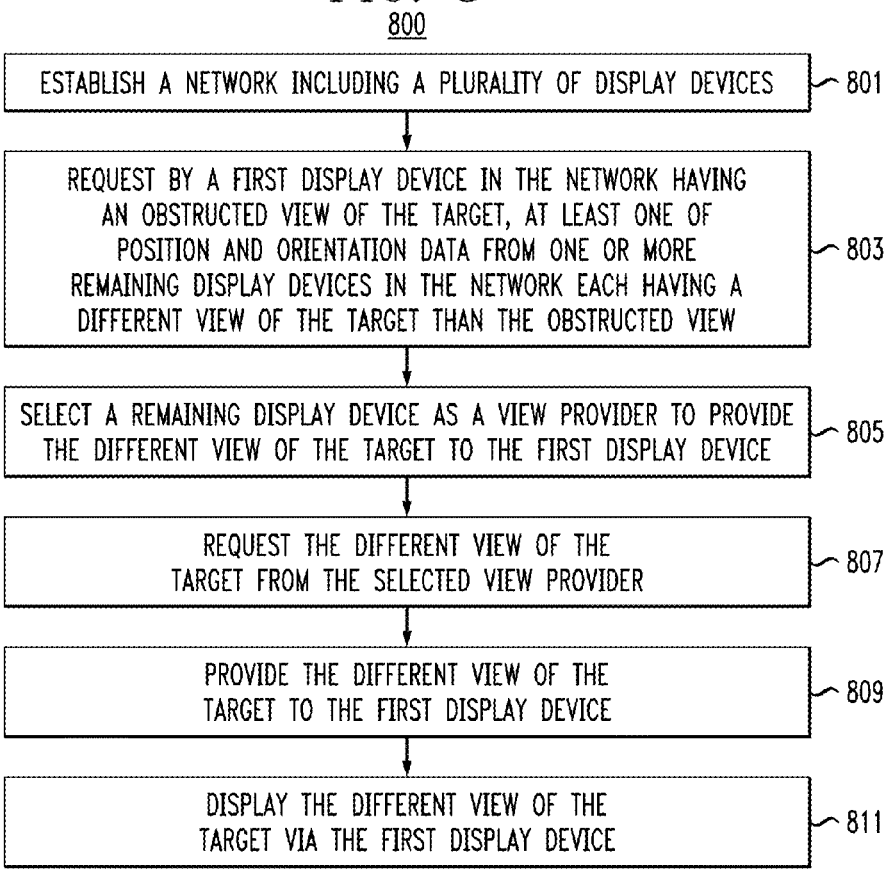

WEARABLE COMPUTING EYEGLASSES THAT PROVIDE UNOBSTRUCTED VIEWS

TECHNICAL FIELD

The field generally relates to enhancing a viewing experience for a user and, in particular, to utilizing communication between wearable computing eyeglasses to provide an unobstructed view of a target.

BACKGROUND

When people attend an event, such as a play, sporting event or a concert, they want to be in a good position to see and enjoy the program. Often, however, their view is completely or partially blocked by objects or other people who are in front of them and/or in their line of sight.

Typically, in order to get a better view, one moves their head and/or body, and/or stands up from their seat. Such movement may, in turn, block the view of people who are behind the individual attempting to secure the better view. In some cases, an event attendee may be constantly shifting their position during a program in an effort to see, and not enjoy the show.

SUMMARY

According to an exemplary embodiment of the present invention, a method for displaying a view of a target comprises establishing a network including a plurality of display devices, requesting by a first display device in the network having an obstructed view of the target, at least one of position and orientation data from one or more remaining display devices in the network each having a different view of the target than the obstructed view, selecting a remaining display device as a view provider to provide the different view of the target to the first display device, requesting the different view of the target from the selected view provider; providing the different view of the target to the first display device, and displaying the different view of the target via the first display device.

According to an exemplary embodiment of the present invention, a system for displaying a view of a target comprises a memory and at least one processor coupled to the memory, wherein the at least one processor is configured to establish a network including a plurality of display devices, request by a first display device in the network having an obstructed view of the target, at least one of position and orientation data from one or more remaining display devices in the network each having a different view of the target than the obstructed view, select a remaining display device as a view provider to provide the different view of the target to the first display device, request the different view of the target from the selected view provider, provide the different view of the target to the first display device, and display the different view of the target via the first display device.

According to an exemplary embodiment of the present invention, a computer program product for displaying a view of a target comprises a computer readable storage medium having program instructions embodied therewith, the program instructions executable by a processor to cause the processor to perform a method comprising establishing a network including a plurality of display devices, requesting by a first display device in the network having an obstructed view of the target, at least one of position and orientation data from one or more remaining display devices in the network each having a different view of the target than the obstructed view, selecting a remaining display device as a view provider to provide the different view of the target to the first display device, requesting the different view of the target from the selected view provider, providing the different view of the target to the first display device, and displaying the different view of the target via the first display device.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which:

FIG. 7 is a flow diagram of a process for displaying a view of a target, according to an exemplary embodiment of the invention.

FIG. 8 is a flow diagram of a process for displaying a view of a target, according to an exemplary embodiment of the invention.

DETAILED DESCRIPTION

Figure 1B:
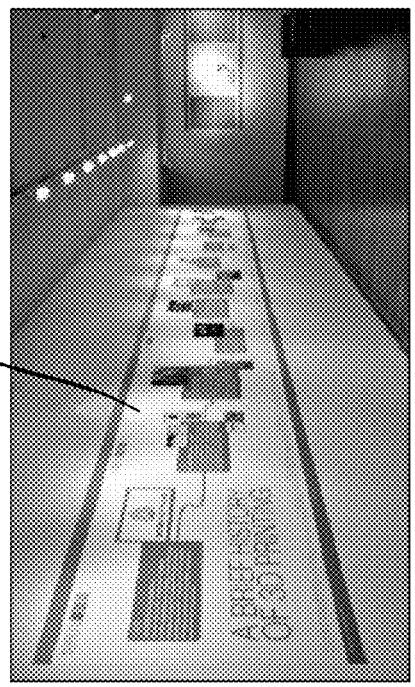
FIGS. 1A and 1B respectively illustrate examples of a view that a person may have of an object or presentation, and a view that can be provided by one or more embodiments of the present invention.

Exemplary embodiments of the invention will now be discussed in further detail with regard to enhancing a viewing experience for a user and, in particular, to utilizing communication between wearable computing eyeglasses to provide an unobstructed view of a target. This invention may, however, be embodied in many different forms and should not be construed as limited to the embodiments set forth herein.

As used herein, the term "real-time" refers to output within strict time constraints. Real-time output can be understood to be instantaneous or in the order of milliseconds or microseconds. Of course, it should be understood that depending on the particular temporal nature of the system in which an embodiment of the invention is implemented, other appropriate timescales that provide at least contemporaneous performance and output can be achieved.

As used herein, the terms "wearable computing eyeglasses," "computing eyewear," and "eyeglasses" can refer to smart glasses, digital eye glasses and/or some other type of wearable computer that can add information to what a wearer sees or provide a complete visual field for a user. The eyeglasses can include, for example, an optical head-mounted display (OHMD), and/or computerized internet-connected glasses with a transparent heads-up display (HUD) or an augmented reality (AR) overlay that may reflect projected digital images. The eyeglasses may be capable of retrieving, processing and storing data, supporting wireless technologies, such as, for example, BLUETOOTH and Wi-Fi, running a mobile operating system and functioning as portable media players to send and play audio and video files. While the embodiments of the present invention are discussed in connection with wearable computing eyeglasses, the embodiments of the present invention are not necessarily limited thereto, and may be applicable to other types of portable computing devices, such as, for example, smart watches, smart phones, tablets, video recording devices and other types of portable display devices that may be used to provide a viewing experience for a user.

In accordance with an embodiment of the present invention, wearable computing eyeglasses worn by a plurality of users at an event can communicate with each other in a decentralized type of wireless network, such as, for example, an ad hoc network within a venue. As used herein, an "ad hoc network" or "wireless ad hoc network (WANET)" can refer to a decentralized type of wireless network that does not rely on a pre-existing infrastructure, such as routers or access points in managed (e.g., infrastructure) wireless networks. As used herein, an ad hoc network or WANET can be a self-configuring, dynamic network which lacks infrastructure setup and administration, enabling devices to independently create and join the network. In the case of a decentralized network, reception, transmission and analysis of data can be performed at each node of the network (e.g., at each pair of wearable eyeglasses).

Alternatively, the wearable computing eyeglasses can communicate with each other in a managed type of network, including but not limited to, a local area network (LAN), wide area network (WAN), cellular network, satellite network or the Internet. The communication can be performed via one or more centralized servers that receive, analyze and send data to and from the wearable computing eyeglasses that are part of the network.

The network communications can be based on relatively close-range communication capabilities, such as, for example, BLUETOOTH and/or near field communication (NFC) capabilities. The embodiments of the present invention are not necessarily limited to BLUETOOTH and/or NFC protocols, and can include other relatively close or longer range protocols, such as, for example, IEEE 802.11, RFID, WiFi, cellular and satellite protocols.

In accordance with an embodiment of the present invention, in response to a request for an unobstructed view received from a first pair of wearable computing eyeglasses (i.e., a view requester), the system automatically selects as a view provider a second pair of wearable computing eyeglasses that is in a better viewing position than the view requester, and transfers a non-blocked view stream from that view provider to the view requester (or at the very least a view stream that is less obstructed than that of the view requester if a fully unobstructed view is not available).

A view requester's eyeglasses may automatically recognize that a view is obstructed and trigger a request for a non-blocked view. For example, a wearer of a pair of computing eyeglasses may be watching a show, when suddenly some objects come up to a view window of the wearer, and block the view of the wearer. The eyeglasses can detect that these objects are not a part of the target. By way of example, if the wearable computing eyeglasses includes a depth camera, the eyeglasses can determine a distance of the obstructing objects from the wearer, and based on typical scenarios, assume that the obstructing objects are closer to the wearer than the target. Alternatively, an eyeglass wearer can manually trigger a request for an unobstructed view (e.g., request on demand).

The non-blocked view can then be displayed in the view requester eyeglasses. In some cases, as described further below, when a view requester's viewing angle is different than that of the view provider, reconstructing a view from a view provider may be required to closely replicate the view requester's viewing angle.

Depending on how a network is configured, in response to a view request, one or more independent servers in communication with each of the nodes of the network can analyze position, orientation, and view streams of potential view providers to automatically determine which of the other wearable computing eyeglasses in the network provides the best matched view for a given view requester, and communicate this determination and best matched view to the view requester. Alternatively, each pair of wearable eyeglasses can be capable of independently analyzing position, orientation, and view streams of potential view providers to determine and choose which of the other wearable computing eyeglasses in the network provides the best matched view for its view request. A best matched view may be, for example, one that has the least or no obstructions, and is closest and/or most similar to the view of the view requester with respect to location and orientation. Other factors for selecting a view provider may include, for example, cost optimization, such as, for example, optimizing network balance (e.g., distribution of load on network devices), optimizing performance of devices in the network and optimizing an ability to provide a real-time view of a target (e.g., with respect to relayed views as described further herein).

Video streaming and transmitting are consuming bandwidth, central processing unit (CPU) power and memory. In order to obtain real-time quality video, the system may need to select an appropriate service provider. The selection process may include, for example, balancing a best view (e.g., the closest viewing angle and position to the view requester) and a best video quality. For example, A and B both request C's view, which may slow down C's performance. In view of the possible slow-down to C performance, the system may decide to assign C's view stream to A, and the view stream of an additional provider, D, to B, even though D does not have the best view for B when compared to C's view. In connection with cost, different view requesters may pay various prices for different viewing experience levels. For example, B may want to always get the best view, and pays a higher price for that privilege than A. In that case, the system can take the different price points into consideration, and distribute the better views to the higher paying customers, and the lower quality views to lower paying customers.

The factors may be weighted based on, for example, their relative importance with respect to providing a worthwhile viewing experience, their effect on the network and whether a geometric transformation should be performed to adapt a view from a different location and/or viewing angle to that of the view requester. Depending on how a network is configured, one or more independent servers in communication with each of the nodes of the network or each pair of wearable eyeglasses can be capable of performing a geometric transformation to adapt a view to a particular location and viewing angle.

According to an embodiment of the present invention, a plurality of possible views from different view providers can be sent to a view requester, and a user wearing the computing eyeglasses can manually select the desired view to use.

In accordance with an embodiment of the present invention, a beacon positioning system or other means of precise indoor/outdoor localization can be incorporated into a network. Position information for each node of a network can be ascertained using, for example, global positioning system (GPS) data. In the event that GPS data may not be precise enough to determine the position of different pairs of wearable eyeglasses in a given network, a more precise localization system, such as a beacon positioning system, can be used to determine locations of network members within, for example, meters, centimeters or micrometers. If a more precise localization system is used, the members of a network will be capable of transmitting and receiving position data to and from a set of location devices (e.g., three or more beacons) located at or near a venue. Beacons can include, for example, cellular base stations, WiFi access points, and radio broadcast towers.

Figure 1A:
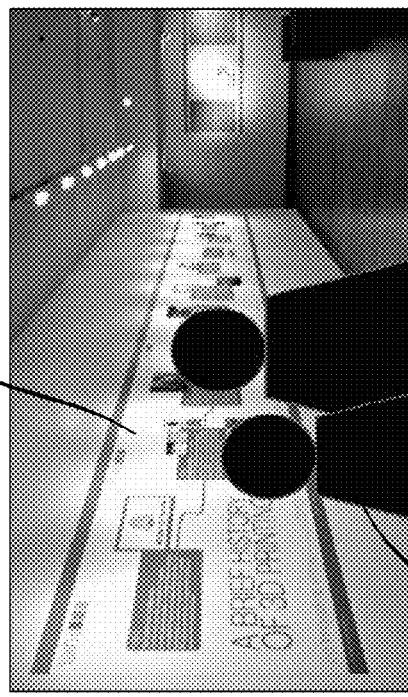

FIGS. 1A and 1B respectively illustrate examples of a view that a person may have of an object or presentation, and a view that can be provided by one or more embodiments of the present invention. As shown in FIG. 1A, the first view includes one or more obstructions 105 preventing a clear view of the object or presentation 110. As shown in FIG. 1B, the one or more obstructions 105 are not part of the view, providing the clear view of the object or presentation 110.

Figure 2:
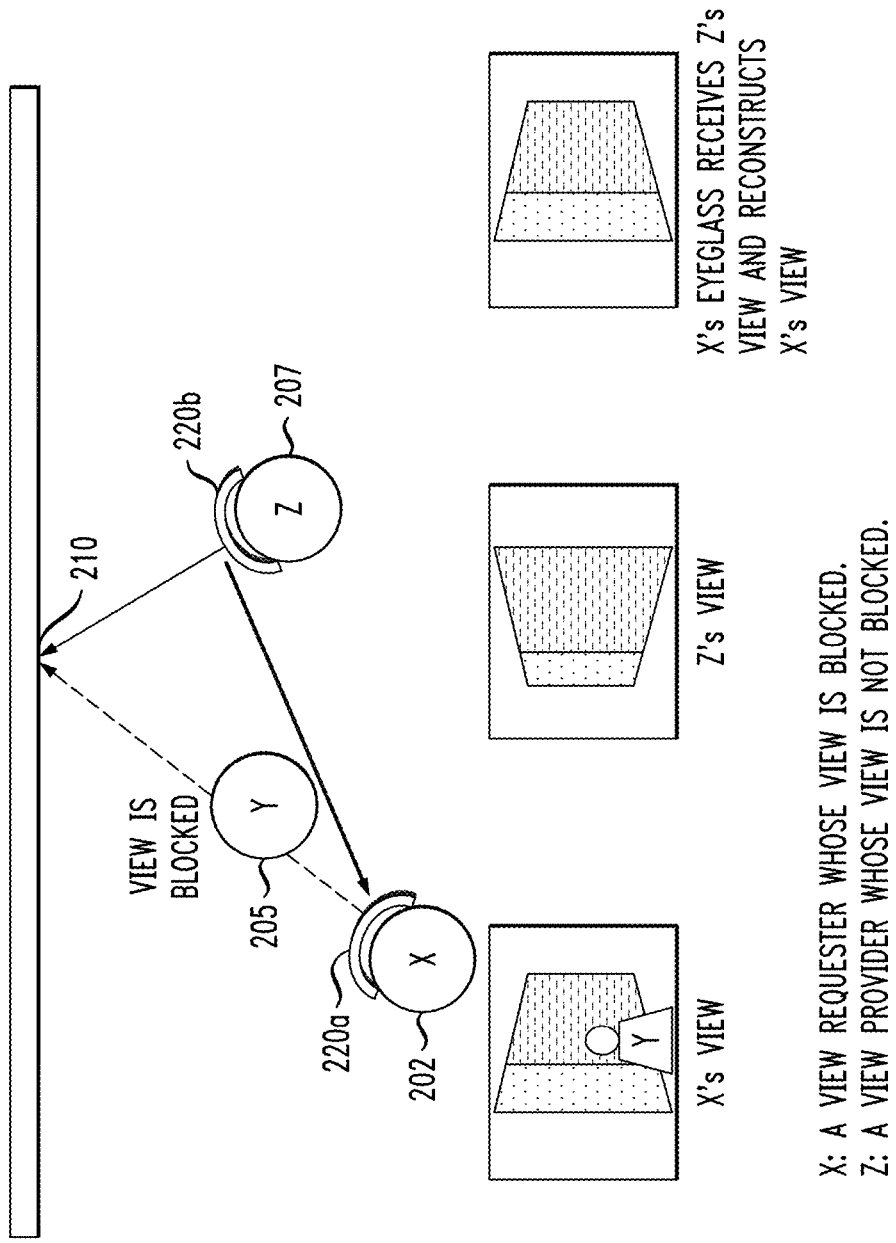
FIG. 2 is a diagram illustrating provision of an unobstructed view, in accordance with an exemplary embodiment of the present invention.

FIG. 2 is a diagram illustrating provision of an unobstructed view, in accordance with an embodiment of the present invention. FIG. 2 depicts one or more viewed objects 210 that are in a two-dimensional plane (e.g., on a wall in an art gallery, smart board, exhibition board, white board, etc.) and user X's view, as shown by the dotted arrow, is partially blocked by an obstruction Y 205. In this case, obstruction Y 205 is shown as a person. However, the embodiments of the present invention are not limited thereto, and can include other types of obstructions, such as, for example, physical objects. In the example in FIG. 2, user X 202 is a view requester whose view is blocked, and user Z 207 is a view provider whose view is not blocked, as shown by the solid arrow pointing to the object(s) 210 from user Z 207. Both user X 202 and user Z 207 are wearing computing eyeglasses 220a and 220b. As can be understood from FIG. 2, user X's view of object(s) 210 is from a left side, and user Z's view of object(s) 210 is from a right side.

Figure 3:
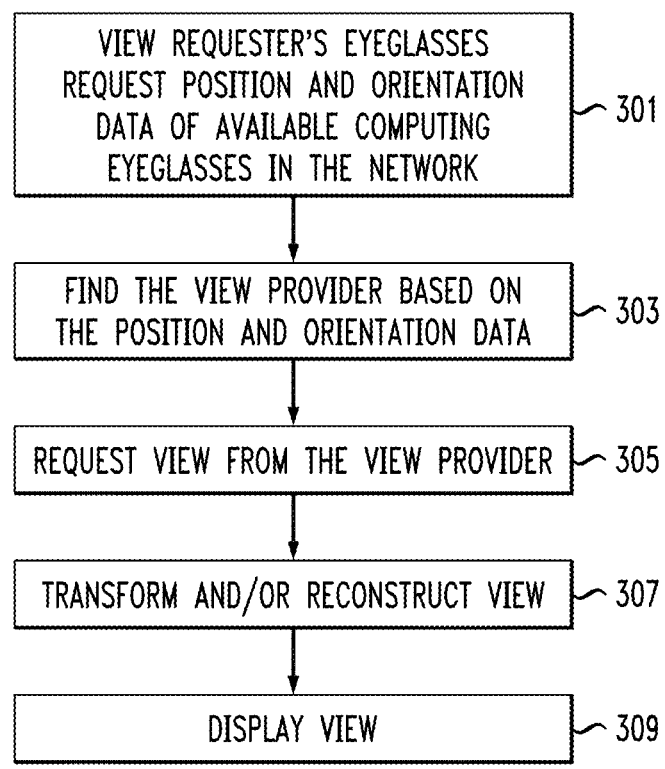
FIG. 3 is a flow diagram of a process for displaying a view of a target, according to an exemplary embodiment of the invention.

In accordance with an embodiment of the present invention, referring to FIGS. 2 and 3, user X's eyeglasses 220a (e.g., the view requester's eyeglasses) request position data (e.g., GPS or local positioning system (LPS) coordinates) and orientation data (e.g., viewing angles) of available computing eyeglasses in the network (block 301). Then, a view provider (user Z 207) is found based on position and orientation data indicating that user Z 207 is viewing the same object(s) 210 as user X 202 (block 303). User X's eyeglasses 220a then request user Z's view from user Z's eyeglasses 220b (block 305). As shown by the solid arrow from user Z 207 to user X 202, user X's eyeglasses 220a receive user Z's view and, if necessary, perform a geometric transformation and/or reconstruction of user Z's view to correspond to user X's position and orientation (block 307). The transformed and/or reconstructed view, or the view as received is then displayed on user X's eyeglasses 220a (block 309).

Figure 4:
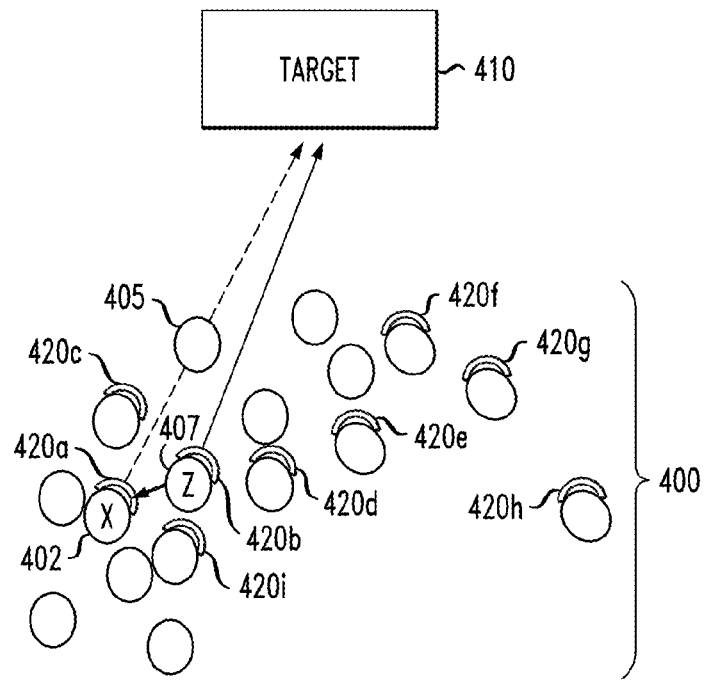
FIG. 4 is a diagram illustrating provision of an unobstructed view, in accordance with an embodiment of the present invention.

FIG. 4 is a diagram illustrating provision of an unobstructed view, in accordance with an embodiment of the present invention. FIG. 4 depicts all or most audience members of a plurality audience members 400 are looking at the same target 410 in a site. For example, the target 410 may include, but is not limited to, a stage on which a performance is occurring, such as a show or concert, or field or court of a sporting event. As can be understood, the objects on the stage, such as performers, instruments, sets, etc. and players on, for example, a field or court, are not necessarily confined to a single plane. Referring to FIG. 4, user X's view of the target 410, as shown by the dotted arrow, is partially blocked by at least obstruction 405. User X's view may be blocked by more than one obstruction. In the example in FIG. 4, user X 402 is a view requester whose view is blocked, and user Z 407 is a view provider whose view is not blocked, as shown by the solid arrow pointing to the target 410 from user Z 407. Both user X 402 and user Z 407 are wearing computing eyeglasses 420a and 420b.

In accordance with an embodiment of the present invention, the system aggregates input from all eyeglasses in the audience (e.g., eyeglasses 420a-420i) to determine what objects at or near a target 410 are included in the vision field that is being viewed by the audience. According to an embodiment, this determination can be performed, using, for example, stereoscopic vision techniques in conjunction with known z-coordinates of audience members.

According to an embodiment of the present invention, the system can detect whether a user's view is unobstructed, and can be a potential view provider. If a view is unobstructed, the system will broadcast information about the view's position, viewing angle, orientation and load (e.g., how many view requesters are currently being serviced with that unobstructed view). If another user's view is blocked, that other user would receive the broadcasted information on each potential view provider, and pick an appropriate view provider.

In accordance with an embodiment of the present invention, multiple audience members other than the view requester (user X 402) are wearing computing eyeglasses 420b-420i. Based on, for example, view stream, location and orientation data received from the eyeglasses 420b-420i, the view requester's (i.e., user X's) eyeglasses 420a pick the view provider (in this case user Z 407) having the most similar and closest viewing perspective to that of user X 402, and which is also unobstructed. User X's eyeglasses 420a request the view stream from user Z's eyeglasses 420b and displays user Z's view stream for user X 402. User Z's view stream may be reconstructed and/or transformed to correspond to the location and orientation of user X 402 with respect to the target 410. In an alternative embodiment, the view requester can manually select a view provider who is closest to the view requester and also has an unobstructed view. The view requester's eyeglasses 420*a* can then request that the view stream of the chosen view provider be transmitted to the eyeglasses 420*a*.

Figure 5:
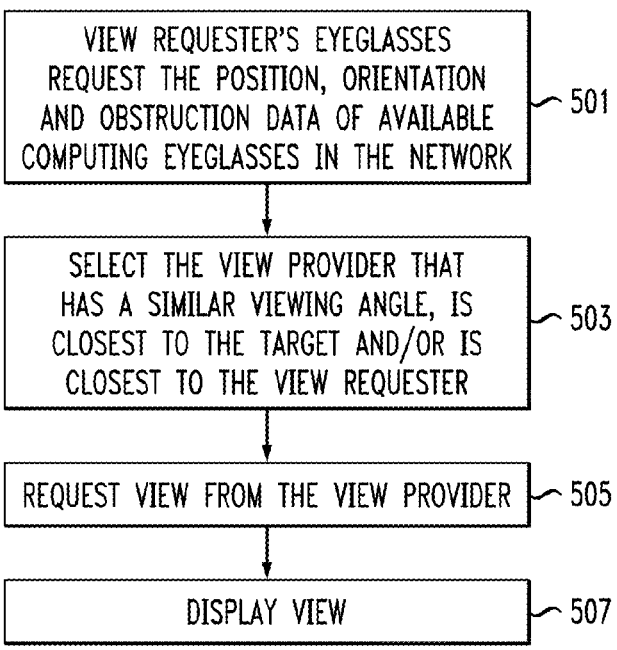
FIG. 5 is a flow diagram of a process for displaying a view of a target, according to an exemplary embodiment of the invention.

In accordance with an embodiment of the present invention, referring to FIGS. 4 and 5, user X's eyeglasses 420*a* request the position and orientation of available computing eyeglasses 420*b*-420*i* in the network, as well as data indicating whether the view of the available computing eyeglasses 420*b*-420*i* is obstructed (block 501).

At block 503, the view requester's eyeglasses 420*a* select the view provider that has a similar viewing angle to the view requester 402, is closest to the target 410 and/or is closest to the view requester. A view from a view provider that has the least or no obstructions can also be included in the selection criteria for a view provider. As noted above, depending on importance, different criteria can be weighted differently when determining which view provider is a best match for the view requester.

At block 505, user X's eyeglasses 420*a* then request the view stream from the selected view stream. The selected view is received and then displayed on user X's eyeglasses 420*a* (block 507).

Figure 6B:
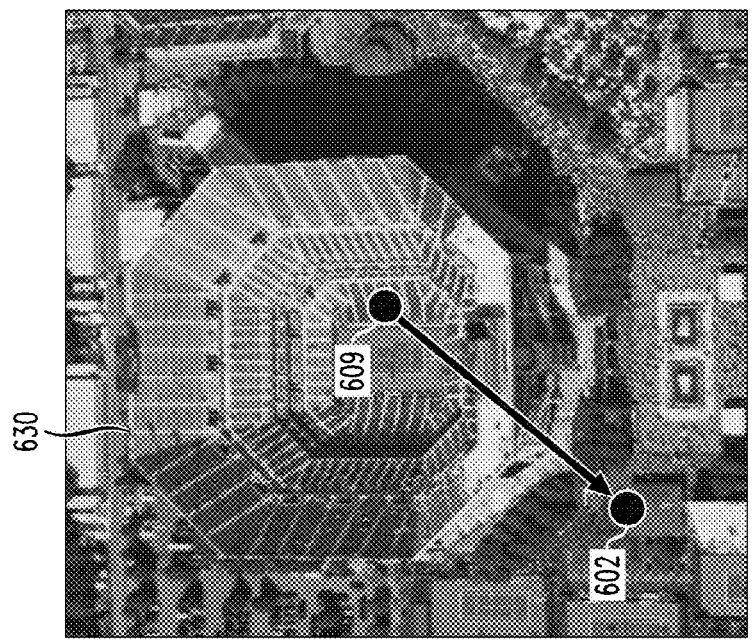
FIG. 6B illustrates a venue including a target and one or more network members inside the venue, and at least one network member outside of the venue, in accordance with an exemplary embodiment of the present invention.
Figure 6A:
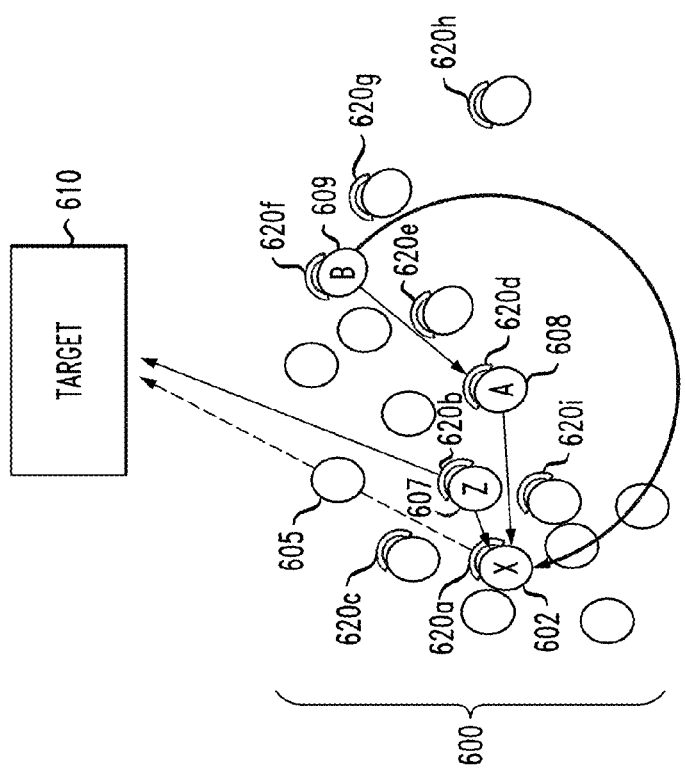
FIG. 6A is a diagram illustrating provision of a plurality of unobstructed views, in accordance with an embodiment of the present invention.

FIG. 6A is a diagram illustrating provision of a plurality of unobstructed views, in accordance with an embodiment of the present invention. Like the embodiment described in connection with FIG. 4, FIG. 6A depicts a plurality of users 600 and a target 610 including, but not limited to, a stage on which a performance is occurring, such as a show or concert, or field of a sporting event. Unlike the embodiment described in connection with FIG. 4, as can be understood from FIG. 6B, all of the plurality of users 600 are not required to be in the site or venue attempting to watch the event. For example, in connection with the embodiment shown in FIG. 6B, the user X 602 may not have been able to purchase a ticket for a tennis match and is located outside the tennis stadium 630. However, user X's eyeglasses 620*a* are receiving a view stream from the eyeglasses 620*f* of user B 609, who is inside the tennis stadium 630 and able to view the match (e.g., target 610). The depiction of user X 602 outside of the venue is only by way of example, and it is to be understood that the features described in connection with FIG. 6A are also applicable when user X is inside the venue.

In connection with the embodiment described in connection with FIGS. 6A and 6B, a plurality of users 600 are wearing computing eyeglasses 620*a*-620*i*. A view requester (e.g., user X 602), whether inside or outside of the venue, can choose any one of the streams from the computing eyeglasses 620*b*-620*i* regardless of their viewing position and orientation, and transfer the selected view to the his/her eyeglasses 620*a*. In accordance with this embodiment, the view requester's (user X's) eyeglasses 620*a* allow the eyeglass wearer to select a pair of computing eyeglasses as the view provider, wherein the computing eyeglasses for selection are not only those with an unobstructed view of the target 610 (e.g., users Z and B 607, 609), but also those eyeglasses (e.g., eyeglasses 620*d* of user A 608) receiving view streams from other eyeglasses. As shown in FIG. 6A, the eyeglasses 620*d* of user A 608 receive the view stream from user B 609, and relay that view stream to user X 602. The relay of views through multiple eyeglasses may result in some delay from a real-time view of the target. However, having a plurality of users each select the same pair eyeglasses with an unobstructed view of the target 610 may result in too much burden on that pair of eyeglasses and exceed its capabilities as a view provider because of having to transmit to too many recipients. To avoid this issue, and potential delay or crashing of the view provider, the burden of transmitting to view requesters can be spread out across multiple eyeglasses in the network. According to an embodiment, taking into consideration, for example, balancing for network performance, load balancing, device performance and real-time effects, the system can suggest view provider eyeglasses (e.g., the eyeglasses 620*d* of user A 608), which can be used to relay a view stream from an original unobstructed view provider (e.g., users Z and B 607, 609), and thereby relieve the original unobstructed view provider of the burden of having to transmit its view stream to every view requester.

In accordance with an embodiment of the present invention, referring to FIGS. 6 and 7, user X's eyeglasses 620*a* request the position, orientation and views of available computing eyeglasses 620*b*-620*i* in the network (block 701). At block 703, as noted above, taking into consideration, for example, balancing for network performance, load balancing, device performance and real-time effects, the system suggest view provider eyeglasses which can be used to relay a view stream from an original unobstructed view provider. The system may also suggest an original unobstructed view provider if conditions permit using the original unobstructed view provider without burdening the original unobstructed view provider. The system may evaluate burden by, for example, evaluating the number of recipients receiving the view stream of the unobstructed view provider, and determining whether the number exceeds a predetermined threshold indicating a burden. In accordance with an embodiment of the present invention, the selection can be performed by one or more servers capable of receiving data from the eyeglasses in the network, including position, orientation, view streams and data regarding transmission links made with other eyeglasses in the network. The one or more servers are operatively connected to the network and to the eyeglasses in the network.

At block 705, the view requester (e.g., user X 602) selects the view provider from the suggested view providers. Alternatively, the view requester's eyeglasses 620*a* automatically select the view provider from the suggested view providers.

At block 707, user X's eyeglasses 620*a* then request the view stream from the selected view provider's eyeglasses. At block 709, user X's eyeglasses 620*a* receive the view stream from the selected view provider's eyeglasses and the received view is then displayed on user X's eyeglasses 620*a*.

FIG. 8 is a flow diagram of a process for displaying a view of a target, according to an exemplary embodiment of the invention. Referring to FIG. 8, the process 800 includes, at block 801, establishing a network including a plurality of display devices. According to an embodiment, the display devices can include computing eyewear, and the network is a wireless ad-hoc network. The process 800 further includes, at block 803, requesting by a first display device in the network having an obstructed view of the target, at least one of position and orientation data from one or more remaining display devices in the network each having a different view of the target than the obstructed view. According to an embodiment, the different view is an unobstructed view of the target.

The process further includes, at block 805, selecting a remaining display device as a view provider to provide the different view of the target to the first display device. The selecting may comprise performing an optimization based on network balance, device performance and/or an ability to provide a real-time view of the target. The selecting can comprise selecting the view provider that has a viewing angle with respect to the target that is closest to the viewing angle with respect to the target of the first display device, is positioned closest to the target and/or is positioned closest to the first display device. Selecting the remaining display device as the view provider can be performed, for example, automatically by the first display device or some other device connected to the network, or manually by a user of the first display device.

The process further includes, at block 807, requesting the different view of the target from the selected view provider and, at block 809, providing the different view of the target to the first display device. Providing the different view of the target to the first display device may comprise relaying the different view from the selected view provider through another remaining display device.

The process 800 further includes, at block 811, displaying the different view of the target via the first display device. The process 800 may further comprise transforming the different view of the target to compensate for differences of at least one of position and orientation with respect to the target between the first display device and the display device selected as the view provider.

The process 800 may also further comprise suggesting one or more remaining display devices as potential view providers, wherein the suggesting is based on at least one of optimizing network balance, optimizing device performance and optimizing an ability to provide a real-time view of the target. According to an embodiment, the process 800 can also include aggregating view data from the plurality of display devices in the network to determine an expanse of the target.

Figure 9:
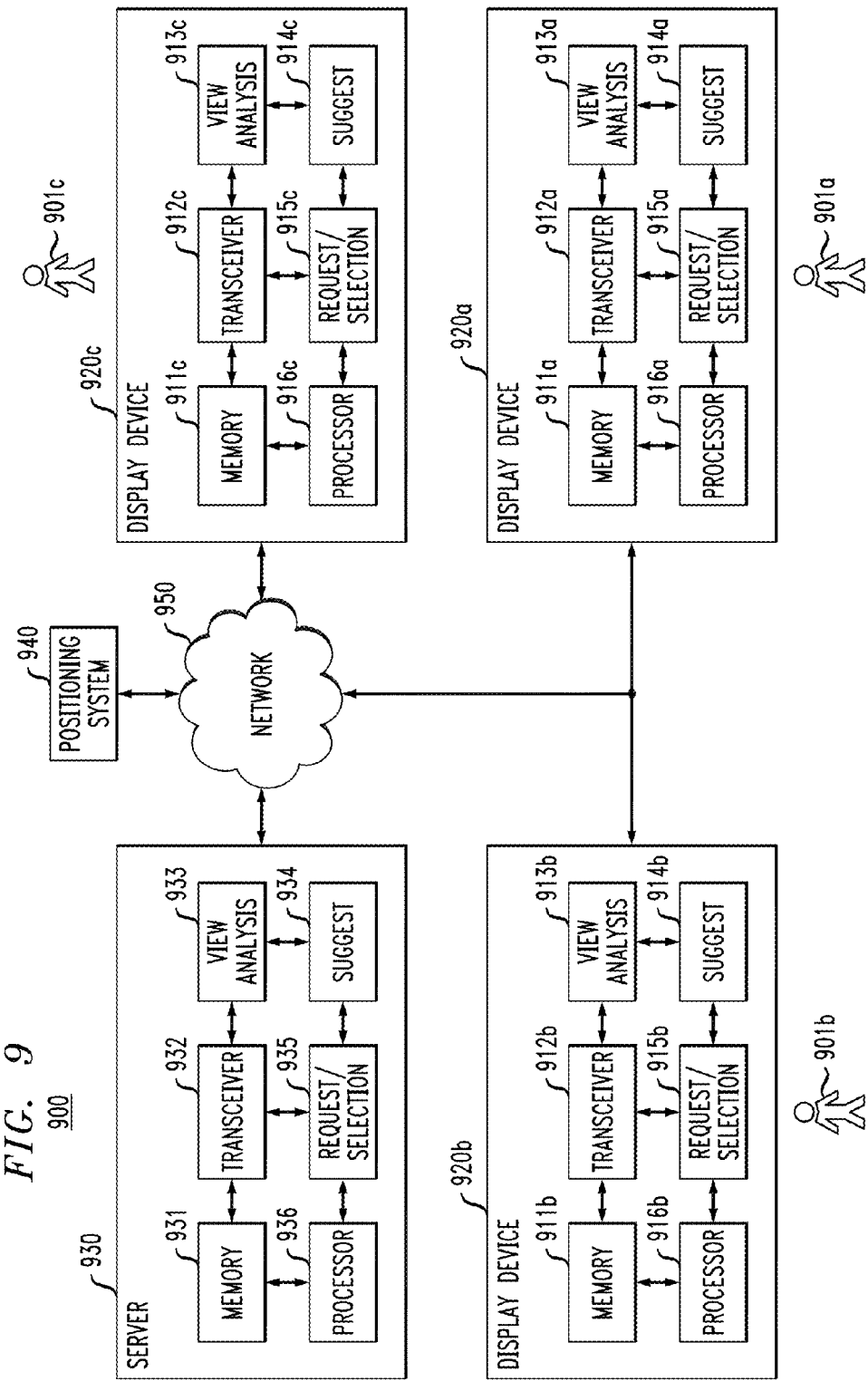
FIG. 9 is a block diagram of a system for displaying a view of a target, according to an exemplary embodiment of the present invention.

FIG. 9 is a block diagram of a system for displaying a view of a target, according to an exemplary embodiment of the present invention. As shown in FIG. 9, the components of the system 900 at least include display devices 920*a*, 920*b* and 920*c*, server 930, positioning system 940 and network 950. It is to be understood that the number of components is merely exemplary, and may be more or less than what is shown. Elements within the display devices 920*a*-920*c* and server, as shown by lines and/or arrows are operatively coupled to each other via, for example, physical connections, such as wired and/or direct electrical contact connections, or wireless connections such as, for example, WiFi, BLUETOOTH, IEEE 802.11 or other wireless conventions. The display devices 920*a*, 920*b* and 920*c*, server 930, and positioning system 940 as shown by lines and/or arrows are operatively coupled to the network 950 via wireless connections such as, for example, WiFi, BLUETOOTH, IEEE 802.11 or other wireless conventions. Alternatively, the display devices 920*a*, 920*b* and 920*c*, server 930, and positioning system 940 may be operatively coupled to the network 950 through some combination of wired and wireless connections. As noted herein, the network 950 can include, but is not limited to, a local area network (LAN), wide area network (WAN), cellular network, ad hoc networks, WANETs, satellite network or the Internet.

Referring to FIG. 9, the system 900 includes the plurality of display devices 920*a*-920*c* as part of the network 950. According to an embodiment, the display devices 920*a*-920*c* can include computing eyewear, worn by users 901*a*, 901*b* and 901*c*, and the network 950 is a wireless ad-hoc network. Using, for example processors 911*a*-*c* and request/section modules 915*a*-915*c*, the display devices, when they have an obstructed view of a target, are configured to request position and/or orientation data from one or more remaining display devices in the network each having a different (e.g., unobstructed) view of the target than the obstructed view. As described herein, requests and other functions that are described as being performed by the display devices can alternatively be routed through and performed by a server 930 having the same or similar functionality to that of the display devices. As can be seen, the server 930 is depicted as having the same or similar components 931, 932, 933, 934, 935 and 936 as the components 911, 912, 913, 914, 915 and 916 of the display devices.

A request/section module 915*a*-915*c* or 935 of a requesting display device or of the server can select one the remaining display devices in the network having the unobstructed view as a view provider to provide the unobstructed view of the target to the view requesting display device. The request/section modules 915*a*-915*c* and 935 may be configured to perform an optimization based on network balance, device performance and/or an ability to provide a real-time view of the target. Based on positioning information provided via the positioning system 940 (e.g., a GPS or LPS) and data provided from view analysis modules 913*a*-*c* or 933, the selecting can comprise selecting the view provider that has a viewing angle with respect to the target that is closest to the viewing angle with respect to the target of the first display device, is positioned closest to the target and/or is positioned closest to the first display device. Selecting the remaining display device as the view provider can be performed, for example, automatically by the requesting display device or some other device connected to the network (e.g., server 930), or manually by a user of the requesting display device.

Using, for example, transceivers 912*a*-*c* or 932, the view of the target from the selected view provider can be requested and provided to the requesting display device. As described herein, providing the view of the target from the view provider to the requesting display device may include relaying the view data from the selected view provider through another remaining display device.

Each display device 920*a*-920*c* is configured to display a view stream of the target for a user of the display device, who is, for example, wearing the display device. Using view analysis modules 913*a*-913*c* or 933 and position data from a positioning system 940, as described herein, it may be necessary to transform a received view of the target to compensate for differences of position and/or orientation with respect to the target between the requesting display device and the display device selected as the view provider.

Suggestion modules 914*a*-*c* or 934 can be configured to suggest display devices as potential view providers, wherein the suggesting is based on at least one of optimizing network balance, optimizing device performance and optimizing an ability to provide a real-time view of the target. According to an embodiment, view analysis modules 913*a*-913*c* or 933 can be configured to aggregate view data from the plurality of display devices in the network to determine an expanse of a target.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 10:
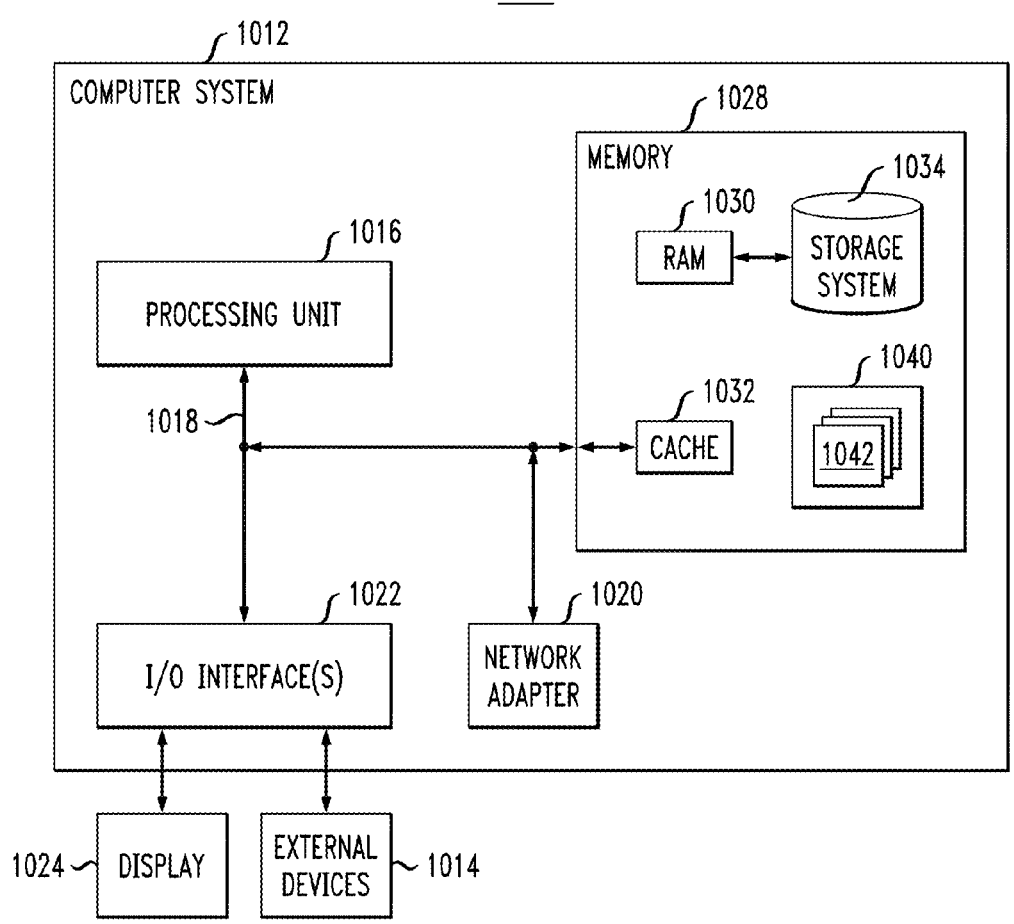
FIG. 10 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 10, in a computing node 1010 there is a computer system/server 1012, which is operational with numerous other general purpose or special purpose computing system environments or configurations. Examples of well-known computing systems, environments, and/or configurations that may be suitable for use with computer system/server 1012 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1012 may be described in the general context of computer system executable instructions, such as program modules, being executed by a computer system. Generally, program modules may include routines, programs, objects, components, logic, data structures, and so on that perform particular tasks or implement particular abstract data types. Computer system/server 1012 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 1012 in computing node 1010 is shown in the form of a general-purpose computing device. The components of computer system/server 1012 may include, but are not limited to, one or more processors or processing units 1016, a system memory 1028, and a bus 1018 that couples various system components including system memory 1028 to processor 1016.

The bus 1018 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 1012 typically includes a variety of computer system readable media. Such media may be any available media that is accessible by computer system/server 1012, and it includes both volatile and non-volatile media, removable and non-removable media.

The system memory 1028 can include computer system readable media in the form of volatile memory, such as random access memory (RAM) 1030 and/or cache memory 1032. The computer system/server 1012 may further include other removable/non-removable, volatile/nonvolatile computer system storage media. By way of example only, storage system 1034 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 1018 by one or more data media interfaces. As depicted and described herein, the memory 1028 may include at least one program product having a set (e.g., at least one) of program modules that are configured to carry out the functions of embodiments of the invention. A program/utility 1040, having a set (at least one) of program modules 1042, may be stored in memory 1028 by way of example, and not limitation, as well as an operating system, one or more application programs, other program modules, and program data. Each of the operating system, one or more application programs, other program modules, and program data or some combination thereof, may include an implementation of a networking environment. Program modules 1042 generally carry out the functions and/or methodologies of embodiments of the invention as described herein.

Computer system/server 1012 may also communicate with one or more external devices 1014 such as a keyboard, a pointing device, a display 1024, etc., one or more devices that enable a user to interact with computer system/server 1012, and/or any devices (e.g., network card, modem, etc.) that enable computer system/server 1012 to communicate with one or more other computing devices. Such communication can occur via Input/Output (I/O) interfaces 1022. Still yet, computer system/server 1012 can communicate with one or more networks such as a local area network (LAN), a general wide area network (WAN), and/or a public network (e.g., the Internet) via network adapter 1020. As depicted, network adapter 1020 communicates with the other components of computer system/server 1012 via bus 1018. It should be understood that although not shown, other hardware and/or software components could be used in conjunction with computer system/server 1012. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 1010 in FIG. 10 can be an example of a cloud computing node. Computing node 1010 is only one example of a suitable cloud computing node and is not intended to suggest any limitation as to the scope of use or functionality of embodiments of the invention described herein. Regardless, computing node 1010 is capable of being implemented and/or performing any of the functionality set forth hereinabove. It is also to be understood that computing node 1010 is not necessarily a cloud computing node.

Figure 11:
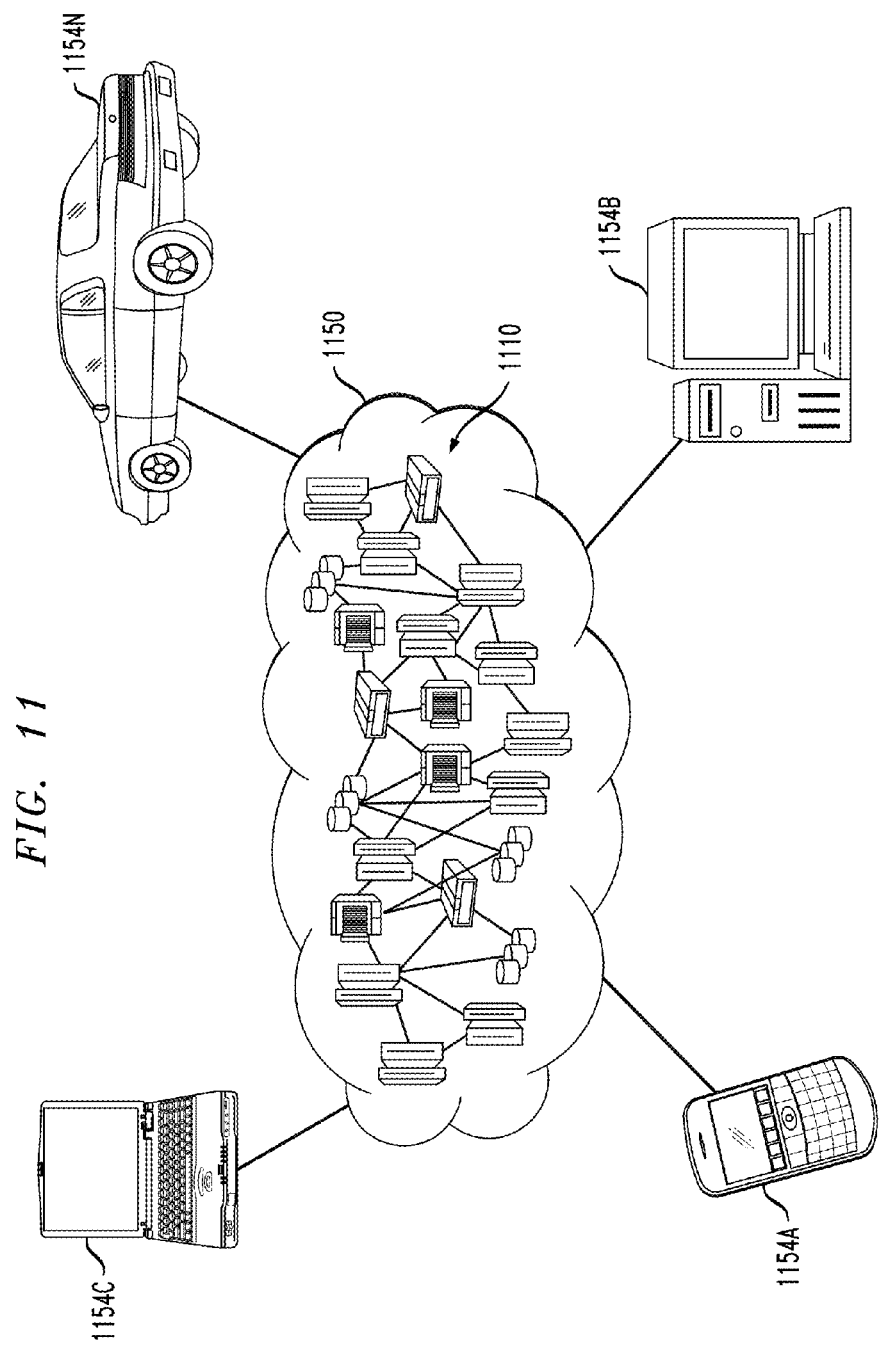
FIG. 11 depicts a cloud computing environment, according to an exemplary embodiment of the present invention.

Referring now to FIG. 11, illustrative cloud computing environment 1150 is depicted. As shown, cloud computing environment 1150 comprises one or more cloud computing nodes 1110 with which local computing devices used by cloud consumers, such as, for example, a wearable device (not explicitly shown), a personal digital assistant (PDA) or cellular telephone 1154A, desktop computer 1154B, laptop computer 1154C, and/or automobile computer system 1154N may communicate. Nodes 1110 may communicate with one another. They may be grouped (not shown) physically or virtually, in one or more networks, such as Private, Community, Public, or Hybrid clouds as described hereinabove, or a combination thereof. This allows cloud computing environment 1150 to offer infrastructure, platforms and/or software as services for which a cloud consumer does not need to maintain resources on a local computing device. It is understood that the types of computing devices 1154A-N shown in FIG. 11 are intended to be illustrative only and that computing nodes 1110 and cloud computing environment 1150 can communicate with any type of computerized device over any type of network and/or network addressable connection (e.g., using a web browser).

Figure 12:
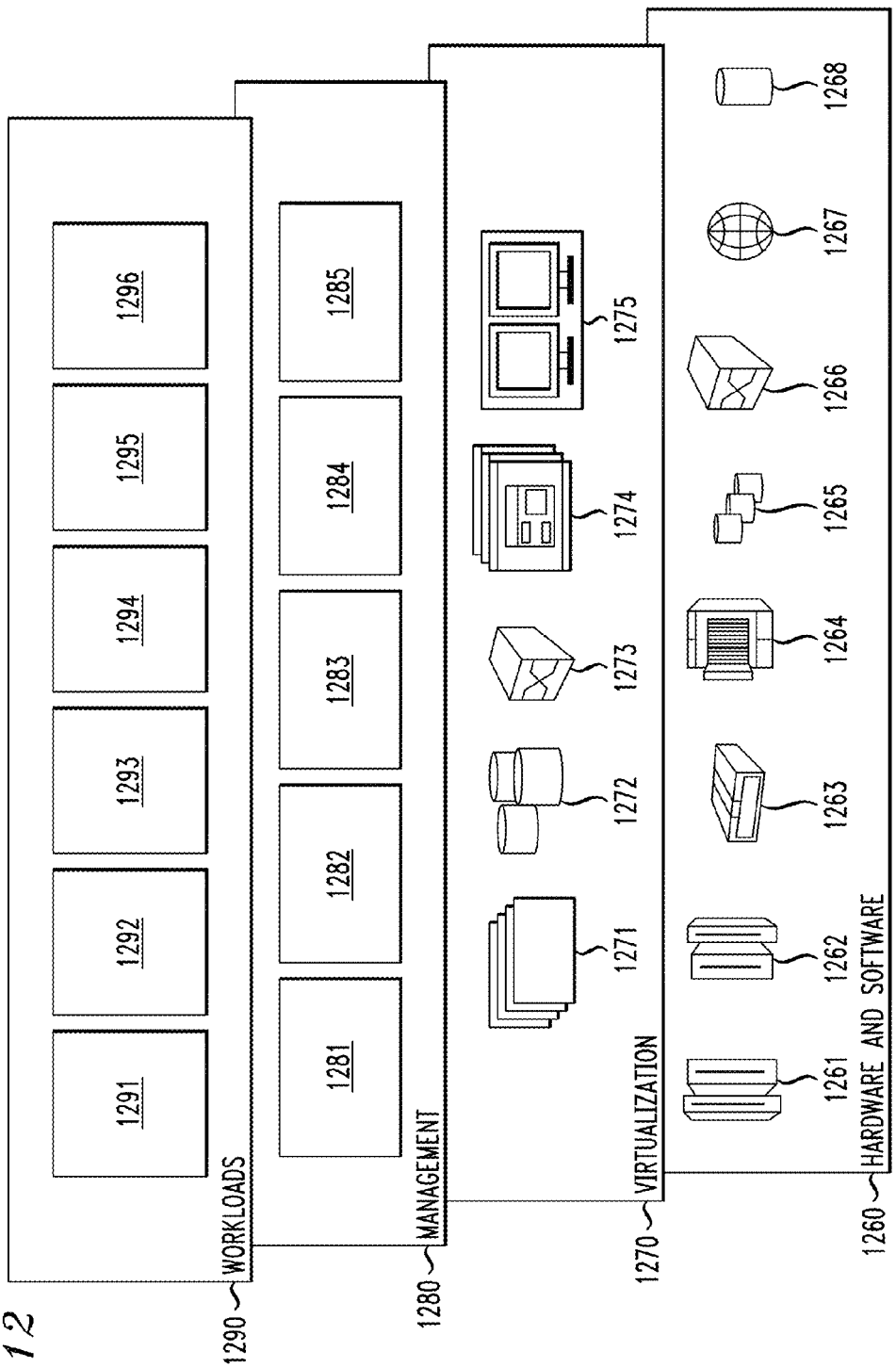
FIG. 12 depicts abstraction model layers, according to an exemplary embodiment of the invention.

Referring now to FIG. 12, a set of functional abstraction layers provided by cloud computing environment 1150 (FIG. 11) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1260 includes hardware and software components. Examples of hardware components include: mainframes 1261; RISC (Reduced Instruction Set Computer) architecture based servers 1262; servers 1263; blade servers 1264; storage devices 1265; and networks and networking components 1266. In some embodiments, software components include network application server software 1267 and database software 1268.

Virtualization layer 1270 provides an abstraction layer from which the following examples of virtual entities may be provided: virtual servers 1271; virtual storage 1272; virtual networks 1273, including virtual private networks; virtual applications and operating systems 1274; and virtual clients 1275.

In one example, management layer 1280 may provide the functions described below. Resource provisioning 1281 provides dynamic procurement of computing resources and other resources that are utilized to perform tasks within the cloud computing environment. Metering and Pricing 1282 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1283 provides access to the cloud computing environment for consumers and system administrators. Service level management 1284 provides cloud computing resource allocation and management such that required service levels are met. Service Level Agreement (SLA) planning and fulfillment 1285 provide pre-arrangement for, and procurement of, cloud computing resources for which a future requirement is anticipated in accordance with an SLA.

Workloads layer 1290 provides examples of functionality for which the cloud computing environment may be utilized. Examples of workloads and functions which may be provided from this layer include: mapping and navigation 1291; software development and lifecycle management 1292; virtual classroom education delivery 1293; data analytics processing 1294; transaction processing 1295; and view providing 1296, which may implement the functionality described above with respect to FIGS. 1-11.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for displaying a view of a target, comprising:
   establishing a network including a plurality of display devices;
   requesting by a first display device in the network having an obstructed view of the target, at least one of position and orientation data from one or more remaining display devices in the network each having a different view of the target than the obstructed view;
   selecting a remaining display device as a view provider to provide the different view of the target to the first display device;
   requesting the different view of the target from the selected view provider;
   providing the different view of the target to the first display device;
   displaying the different view of the target via the first display device; and
   transforming the different view of the target to compensate for differences of at least one of position and orientation with respect to the target between the first display device and the display device selected as the view provider;
   wherein the method is performed by at least one computer system comprising at least one memory and at least one processor coupled to the memory.

2. The method according to claim 1, wherein the different view is an unobstructed view of the target.

3. The method according to claim 1, wherein the display devices include computing eyewear.

4. The method according to claim 1, wherein the network is a wireless ad-hoc network.

5. The method according to claim 1, wherein the selecting comprises performing an optimization based on at least one of network balance, device performance and an ability to provide a real-time view of the target.

6. The method according to claim 1, wherein the selecting comprises selecting the view provider that at least one of has a viewing angle with respect to the target that is closest to the viewing angle with respect to the target of the first display device, is positioned closest to the target and is positioned closest to the first display device.

7. The method according to claim 1, further comprising suggesting one or more remaining display devices as potential view providers.

8. The method according to claim 7, wherein the suggesting is based on at least one of optimizing network balance, optimizing device performance and optimizing an ability to provide a real-time view of the target.

9. A method for displaying a view of a target, comprising:
   establishing a network including a plurality of display devices;
   requesting by a first display device in the network having an obstructed view of the target, at least one of position and orientation data from one or more remaining display devices in the network each having a different view of the target than the obstructed view;
   selecting a remaining display device as a view provider to provide the different view of the target to the first display device;
   requesting the different view of the target from the selected view provider;
   providing the different view of the target to the first display device; and
   displaying the different view of the target via the first display device;
   wherein providing the different view of the target to the first display device comprises relaying the different view from the selected view provider through another remaining display device; and
   wherein the method is performed by at least one computer system comprising at least one memory and at least one processor coupled to the memory.

10. The method according to claim 1, wherein selecting the remaining display device as the view provider is performed by the first display device.

11. The method according to claim 1, wherein selecting the remaining display device as the view provider is performed by a user of the first display device.

12. The method according to claim 1, further comprising aggregating view data from the plurality of display devices in the network to determine an expanse of the target.

13. A system for displaying a view of a target, comprising:
    a memory and at least one processor coupled to the memory, wherein the at least one processor is configured to:
      establish a network including a plurality of display devices;
      request by a first display device in the network having an obstructed view of the target, at least one of position and orientation data from one or more remaining display devices in the network each having a different view of the target than the obstructed view;
      select a remaining display device as a view provider to provide the different view of the target to the first display device;
      request the different view of the target from the selected view provider;
      provide the different view of the target to the first display device;
      display the different view of the target via the first display device; and
      transform the different view of the target to compensate for differences of at least one of position and orientation with respect to the target between the first display device and the display device selected as the view provider.

14. The system according to claim 13, wherein the different view is an unobstructed view of the target.

15. The system according to claim 13, wherein the selecting comprises selecting the view provider that at least one of has a viewing angle with respect to the target that is closest to the viewing angle with respect to the target of the first display device, is positioned closest to the target and is positioned closest to the first display device.

16. The system according to claim 13, wherein the at least one processor is further configured to suggest one or more remaining display devices as potential view providers, wherein the suggesting is based on at least one of optimizing network balance, optimizing device performance and optimizing an ability to provide a real-time view of the target.

17. A system for displaying a view of a target, comprising:
    a memory and at least one processor coupled to the memory, wherein the at least one processor is configured to:
      establish a network including a plurality of display devices;
      request by a first display device in the network having an obstructed view of the target, at least one of position and orientation data from one or more remaining display devices in the network each having a different view of the target than the obstructed view;

select a remaining display device as a view provider to provide the different view of the target to the first display device;

request the different view of the target from the selected view provider;

provide the different view of the target to the first display device; and display the different view of the target via the first display device;

wherein providing the different view of the target to the first display device comprises relaying the different view from the selected view provider through another remaining display device.

18. A computer program product for displaying a view of a target, the computer program product comprising a computer readable storage medium having program instructions embodied therewith, the program instructions executable by a processor to cause the processor to perform a method comprising:

establishing a network including a plurality of display devices;

requesting by a first display device in the network having an obstructed view of the target, at least one of position and orientation data from one or more remaining display devices in the network each having a different view of the target than the obstructed view;

selecting a remaining display device as a view provider to provide the different view of the target to the first display device;

requesting the different view of the target from the selected view provider;

providing the different view of the target to the first display device;

displaying the different view of the target via the first display device; and transforming the different view of the target to compensate for differences of at least one of position and orientation with respect to the target between the first display device and the display device selected as the view provider.

* * * * *